United States Patent
Harding (10) Patent No.: US 7,711,086 B2
(45) Date of Patent: May 4, 2010

(54) SYSTEMS FOR IMPROVING A SPATIAL RESOLUTION OF AN IMAGE

(75) Inventor: Geoffrey Harding, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 0 days.

(21) Appl. No.: 12/074,900

(22) Filed: Mar. 7, 2008

(65) Prior Publication Data
US 2009/0225943 A1   Sep. 10, 2009

(51) Int. Cl.
   *G01N 23/04* (2006.01)
(52) U.S. Cl. .......................................... 378/62; 378/145
(58) Field of Classification Search ............... 378/4–20, 378/51, 62, 145–150
   See application file for complete search history.

(56) References Cited

U.S. PATENT DOCUMENTS 4,891,833 A * 1/1990 Bernardi ..................... 378/145
7,369,640 B2 * 5/2008 Seppi et al. ..................... 378/9

OTHER PUBLICATIONS

Geoffrey Harding, U.S. Appl. No. 12/005,794, "Method, a Processor, and a System for Identifying a Substance," filed Dec. 28, 2007.
Geoffrey Harding et al., U.S. Appl. No. 12/005,843, "Systems and Methods for Reducing a Degradation Effect on a Signal," filed Dec. 28, 2007.
Geoffrey Harding, U.S. Appl. No. 12/006,010, "System and Methods for Characterizing a Substance," filed Dec. 28, 2007.
Geoffrey Harding, U.S. Appl. No. 12/006,140, "Method, a Processor, and a System for Tracking a Focus of a Beam," filed Dec. 31, 2007.
Robert E. Alvarez and Albert Macovski, "Energy-selective Reconstructions in X-ray Computerized Tomography," Phys. Med. Biol. 1976, vol. 21, No. 5, 733-744.

* cited by examiner

*Primary Examiner*—Jurie Yun
(74) *Attorney, Agent, or Firm*—Armstrong Teasdale LLP (57) ABSTRACT

Systems for improving a spatial resolution of an image are described. One of the systems includes an X-ray source configured to generate X-rays, a transmission detector configured to detect the X-rays to output a plurality of electrical signals, and a plate configured to improve the spatial resolution upon receiving the X-rays. The plate is configured to output a fan-beam upon receiving the X-rays.

20 Claims, 5 Drawing Sheets

SYSTEMS FOR IMPROVING A SPATIAL RESOLUTION OF AN IMAGE

FIELD OF THE INVENTION

The field of the invention relates generally to systems for improving a quality of an image and, more particularly, to systems for improving a spatial resolution of an image.

BACKGROUND OF THE INVENTION

The events of Sep. 11, 2001 instigated an urgency for more effective and stringent screening of airport baggage. The urgency for security expanded from an inspection of carry-on bags for knives and guns to a complete inspection of checked bags for a range of contraband with particular emphasis upon concealed explosives. X-ray imaging systems including a computed tomography (CT) system are currently employed for screening.

The CT system includes an X-ray source that generates X-rays that pass through a material. The CT system further includes a detector that detects the X-rays to create a plurality of signals. The CT system also includes a computer that generates an image of the material from the signals. However, a resolution of the image may not have a suitable quality to enable identifying the material as a threat material.

Identification systems based on X-ray diffraction (XRD) techniques provide an improved discrimination of the material compared to that provided by the X-ray imaging systems. The XRD identification systems measure d-spacings between lattice planes of micro-crystals in the material. A "d-spacing" is a perpendicular distance between adjacent lattice planes in the material. However, if the XRD identification systems include the detector and the computer mentioned above, the XRD identification systems may generate an image that is not of suitable quality. Accordingly, the diffraction techniques may suffer from a high false alarm rate for some classes of substances.

BRIEF DESCRIPTION OF THE INVENTION

A brief description of embodiments of systems for improving a spatial resolution of an image follows.

In one aspect, a system for improving a spatial resolution of an image is described. The system includes an X-ray source configured to generate X-rays, a transmission detector configured to detect the X-rays to output a plurality of electrical signals, and a plate configured to improve the spatial resolution upon receiving the X-rays. The plate is configured to output a fan-beam upon receiving the X-rays.

In another aspect, a system for improving a spatial resolution of an image is described. The system includes an X-ray source configured to generate X-rays, a transmission detector configured to detect the X-rays, and a plate positioned between the X-ray source and the transmission detector. The plate is configured to improve the spatial resolution of the image upon receiving the X-rays.

In yet another aspect, a system for improving a spatial resolution of an image is described. The system includes a plurality of X-ray sources arranged along an arc and configured to generate X-rays that are incident on a substance, a transmission detector configured to detect the X-rays, and a plate positioned between the substance and the transmission detector. The plate is configured to improve the spatial resolution of the image.

BRIEF DESCRIPTION OF THE DRAWINGS

FIGS. 1-7 show embodiments of systems for improving a spatial resolution of an image.

DETAILED DESCRIPTION OF THE INVENTION

While described in terms of detecting contraband including, without limitation, weapons, explosives, and/or narcotics, within baggage, the embodiments described herein can be used for any suitable imaging application.

Figure 1:
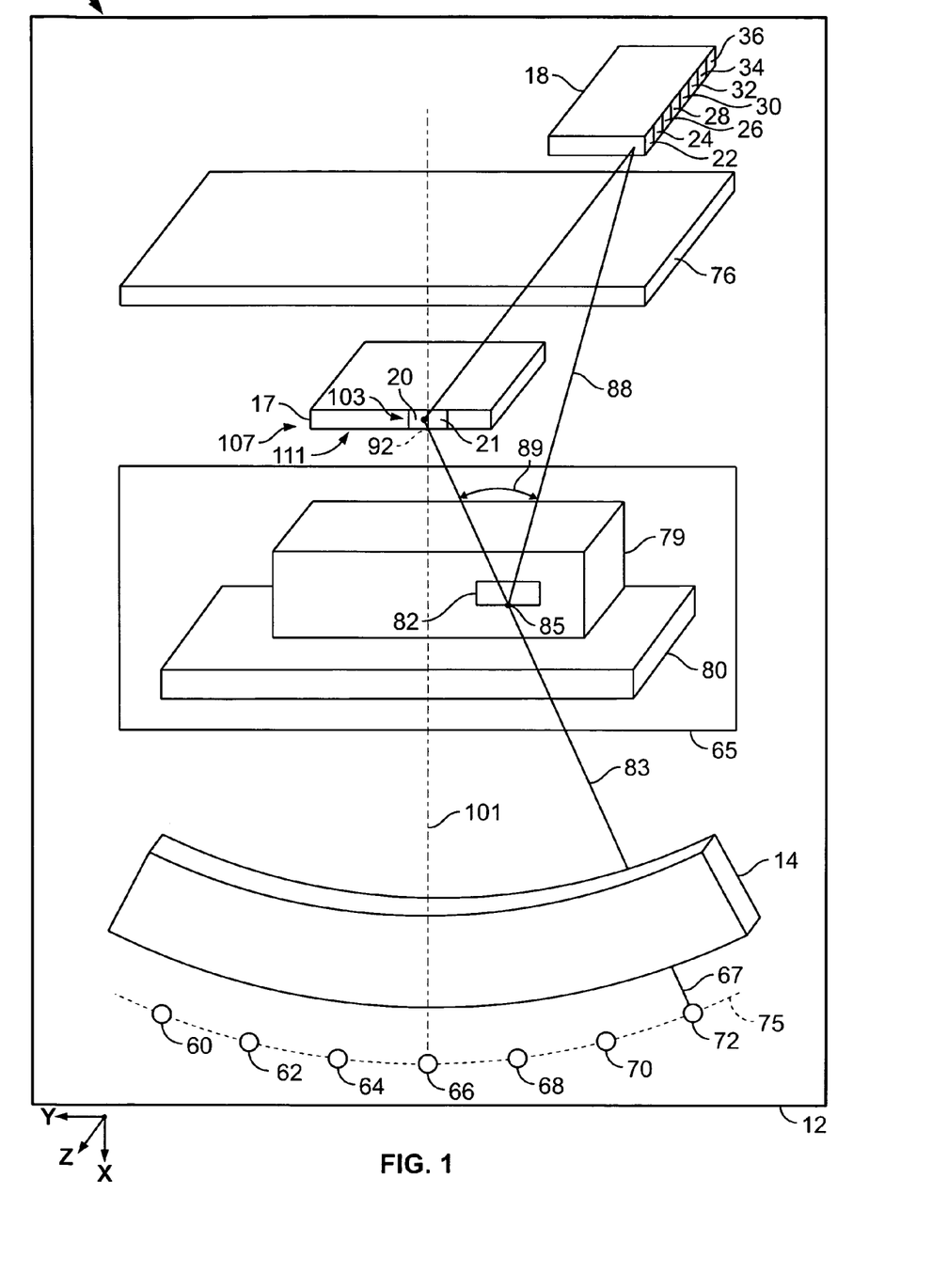
FIG. 1 is an isometric view of an embodiment of a system for improving a spatial resolution of an image.

FIG. 1 is an isometric view of a block diagram of an embodiment of a system 10 for improving a spatial resolution of an image. System 10 includes a gantry 12. Gantry 12 includes a primary collimator 14, a transmission detector 17, and a scatter detector 18.

Transmission detector 17 includes a plurality of detector elements, such as detector elements 20 and 21. Scatter detector 18 is a segmented semiconductor detector. An example of scatter detector 18 includes a segmented detector fabricated from Germanium. Scatter detector 18 includes a plurality of detector cells or detector elements 22, 24, 26, 28, 30, 32, 34, and 36 for detecting coherent scatter. Scatter detector 18 includes any number, such as, ranging from and including 5 to 1200, of detector elements. For example, scatter detector 18 includes 5 detector elements in a z-direction parallel to a z-axis, and one detector element in a y-direction parallel to a y-axis. As another example, scatter detector 18 includes 20 detector elements in the z-direction, and 20 detector elements in the y-direction. As yet another example, scatter detector 18 includes 40 detector elements in the z-direction, and 30 detector elements in the y-direction. An x-axis, the y-axis, and the z-axis are located within an xyz co-ordinate system having an origin. The x-axis is perpendicular to the y-axis and the z-axis, and the y-axis is perpendicular to the z-axis, and the x-axis is parallel to an x-direction.

Scatter detector 18 and transmission detector 17 may be located in the same yz plane. A yz plane is formed by the y-axis and the z-axis. Scatter detector 18 is separate from transmission detector 17 by a shortest distance ranging from and including 30 millimeters (mm) to 60 mm in the z-direction. As an example, scatter detector 18 is separated from transmission detector 17 by a shortest distance of 35 mm in the z-direction. As another example, scatter detector 18 is separated from transmission detector 17 by a shortest distance of 50 mm in the z-direction. As yet another example, scatter detector 18 is separated from transmission detector 17 by a shortest distance of 60 mm in the z-direction.

Secondary collimator 76 includes a number of collimator elements, such as sheets, plates, or laminations. The collimator elements of scatter detector 18 are made of a secondary collimator material, which is a radiation-absorbing material, such as steel, copper, silver, or tungsten.

Gantry 12 further includes a plurality of X-ray sources 60, 62, 64, 66, 68, 70, and 72, and a secondary collimator 76. An example of each X-ray source 60, 62, 64, 66, 68, 70, and 72 includes a polychromatic X-ray source. X-ray sources 60, 62, 64, 66, 68, 70, and 72, and transmission detector 17 form an inverse single-pass multi-focus imaging system (MFXS). X-ray sources 60, 62, 64, 66, 68, 70, 72, and 74 have an inverse fan-beam geometry that includes a symmetric location of the X-ray sources relative to the x and z axes.

X-ray sources 60, 62, 64, 66, 68, 70, 72, and 74 are located along an arc 75. X-ray sources 60, 62, 64, 66, 68, 70, and 72 are located parallel to and coincident with arc 75. Each X-ray source 60, 62, 64, 66, 68, 70, and 72 includes a cathode and an anode. Alternatively, each X-ray source 60, 62, 64, 66, 68, 70, and 72 includes a cathode and all X-ray sources 60, 62, 64, 66, 68, 70, and 72 share a common anode. A focus of an anode has a width ranging from and including 1 mm to 50 mm in the y-direction. For example, a focus of an anode has a width of 1 mm in the y-direction. As another example, a focus of an anode has a width of 25 mm in the y-direction. As yet another example, a focus of an anode has a width of 50 mm in the y-direction.

Detector element 20 is located at a position 103 with respect to the origin. Position 103 includes an x-axis position along the x-axis, a y-axis position along the y-axis, and a z-axis position along the z-axis. Transmission detector 17 is located at an x-axis position 107, along the x-axis, from the origin and has a surface 111. Surface 111 faces container 79 and is parallel to a yz plane.

A container 79 is placed on a support 80 between X-ray sources 60, 62, 64, 66, 68, 70, and 72, and scatter detector 18. Container 79 and support 80 are located within an opening 65 of gantry 12. Non-limiting examples of container 79 include a bag, a box, and an air cargo container. Container 79 includes a substance 82. Non-limiting examples of substance 82 include an organic explosive, an amorphous substance having a crystallinity of less than twenty five percent, a quasi-amorphous substance having a crystallinity at least equal to twenty-five percent and less than fifty percent, a partially crystalline substance having a crystallinity at least equal to fifty percent and less than one-hundred percent, and a crystalline substance having a crystallinity of one-hundred percent. A gel explosive is a non-limiting example of the amorphous substance, a slurry explosive is a non-limiting example of the quasi-amorphous substance, and a special nuclear material and an explosive including ammonium nitrate are non-limiting examples of the partially crystalline substance. Non-limiting examples of the special nuclear material include plutonium and uranium. Non-limiting examples of support 80 include a table and a conveyor belt. Secondary collimator 76 is located between support 80 and scatter detector 18.

X-ray source 72 emits an X-ray beam 67 in an energy range, which is dependent on a voltage applied by a power source to X-ray source 72. Primary collimator 14 outputs a primary beam 83, such as a converging beam, after collimating X-ray beam 67. Primary beam 83 is incident on a point 85 of substance 82 within container 79 arranged on support 80 to generate scattered radiation including a scattered beam 88. Primary beam 83 is further incident on an area 92 of detector element 20. Area 92 is a focal spot of primary beam 83 incident on surface 111 of transmission detector 17. Area 92 has a width that may range from and including 9 mm to 11 mm in the y-direction and a length from and including 9 mm to 11 mm in the z-direction. For example, area 92 has a width of 9 mm in the y-direction and a length of 9 mm in the z-direction. As another example, area 92 has a width of 10 mm in the y-direction and a length of 10 mm in the z-direction. As yet another example, area 92 has a width of 11 mm in the y-direction and a length of 11 mm in the z-direction.

Transmission detector 17 is located at a focus of primary collimator 14. For example, primary beam 83 output from primary collimator 14 converges at the centroid of transmission detector 17. As another example, primary beam 83 converges at area 92. Scattered beam 88 forms a scatter angle value 89 with respect to primary beam 83. Secondary collimator 76 collimates a portion of the scattered radiation to output the remaining portion of the scattered radiation and the remaining portion includes scattered beam 88.

Above support 80, there is arranged transmission detector 17, which measures an intensity of primary beam 83. Moreover, above support 80, there is arranged scatter detector 18 that measures photon energies of the remaining portion of the scattered radiation received by scatter detector 18. Scatter detector 18 measures a plurality of X-ray photons within the remaining portion of the scattered radiation in an energy-sensitive manner by outputting a plurality of electrical output signals linearly dependent on a plurality of energies of the X-ray photons detected from within the remaining portion of the scattered radiation. Scatter detector 18 detects the remaining portion, including scattered beam 88, of the scattered radiation output from secondary collimator 76 to output a plurality of electrical signals.

In an alternative embodiment, gantry 12 includes more than one scatter detector 18. For example, gantry 12 includes an additional scatter detector that may lie in the same yz plane as that of scatter detector 18 and may have the same number of detector elements as scatter detector 18. In yet another alternative embodiment, gantry 12 includes more than one transmission detector 17.

Figure 2:
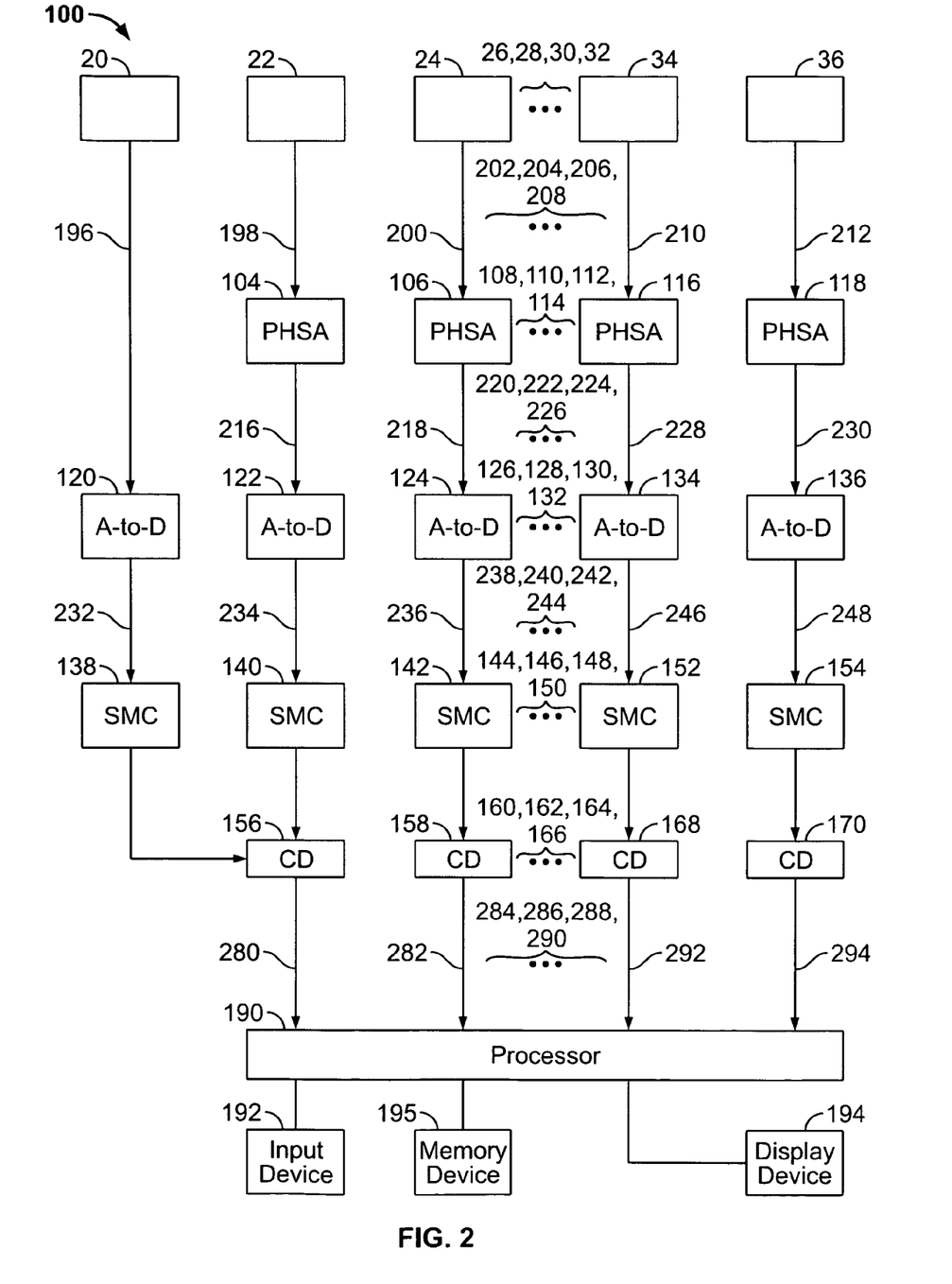
FIG. 2 is block diagram of an embodiment of a system for improving a spatial resolution of an image.

FIG. 2 is block diagram of an embodiment of a system 100 for characterizing a substance. System 100 includes detector element 20 of transmission detector 17, scatter detector elements 22, 24, 26, 28, 30, 32, 34, and 36, a plurality of pulse-height shaper amplifiers (PHSA) 104, 106, 108, 110, 112, 114, 116, and 118, a plurality of analog-to-digital (A-to-D) converters 120, 122, 124, 126, 128, 130, 132, 134, and 136, a plurality of spectrum memory circuits (SMCs) 138, 140, 142, 144, 146, 148, 150, 152, and 154 allowing pulse height spectra to be acquired, a plurality of correction devices (CDs) 156, 158, 160, 162, 164, 166, 168, and 170, a processor 190, an input device 192, a display device 194, and a memory device 195. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer may include a device, such as a floppy disk drive or CD-ROM drive, for reading data from a computer-readable medium, such as a floppy disk, a compact disc-read only memory (CD-ROM), a magneto-optical disk (MOD), and/or a digital versatile disc (DVD). In an alternative embodiment, processor 190 executes instructions stored in firmware. Non-limiting examples of display device 194 include a liquid crystal display (LCD) and a cathode ray tube (CRT). Non-limiting examples of input device 192 include a mouse and a keyboard. Non-limiting examples of memory device 195 include a random access memory (RAM) and a read-only memory (ROM). An example of each correction device 156, 158, 160, 162, 164, 166, 168, and 170 includes a divider circuit. Each spectrum memory circuit 138, 140, 142, 144, 146, 148, 150, 152, and 154 includes an adder and a memory device, such as a RAM or a ROM.

Detector element 20 is coupled to analog-to-digital converter 120, and detector elements 22, 24, 26, 28, 30, 32, 34, and 36 are coupled to pulse-height shaper amplifiers 104, 106, 108, 110, 112, 114, 116, and 118, respectively. Detector element 20 generates an electrical output signal 196 by detecting X-rays, such as primary beam 83 (shown in FIG. 1), and detector elements 22, 24, 26, 28, 30, 32, 34, and 36 generate a plurality of electrical output signals 198, 200, 202, 204, 206, 208, 210, and 212 by detecting scattered radiation, such as scattered beam 88 (shown in FIG. 1). For example, detector element 22 generates electrical output signal 198 for each scattered X-ray photon incident on detector element 22. Each pulse-height shaper amplifier amplifies an electrical output signal received from a corresponding detector element. For example, pulse-height shaper amplifier 104 amplifies electrical output signal 198 and pulse-height shaper amplifier 106 amplifies electrical output signal 200. Pulse-height shaper amplifiers 104, 106, 108, 110, 112, 114, 116, and 118 have a gain factor determined by processor 190.

An amplitude of an electrical output signal output from a detector element is proportional to an energy of an X-ray quantum that is detected by the detector element to generate the electrical output signal. For example, an amplitude of electrical output signal 196 is proportional to an energy of an X-ray quantum in X-rays, such as primary beam 83 (shown in FIG. 1), detected by detector element 20. As another example, an amplitude of electrical output signal 198 is proportional to an energy of an X-ray quantum within scattered radiation that is detected by detector element 22.

A pulse-height shaper amplifier generates an amplified output signal by amplifying an electrical output signal generated from a detector element. For example, pulse-height shaper amplifier 104 generates an amplified output signal 216 by amplifying electrical output signal 198 and pulse-height shaper amplifier 106 generates an amplified output signal 218 by amplifying electrical output signal 200. Similarly, a plurality of amplified output signals 220, 222, 224, 226, 228, and 230 are generated. An analog-to-digital converter converts an output signal from an analog form to a digital form to generate a digital output signal. For example, analog-to-digital converter 120 converts electrical output signal 196 from an analog form to a digital format to generate a digital output signal 232, and analog-to-digital converter 122 converts amplified output signal 216 from an analog form to a digital format to generate a digital output signal 234. Similarly, a plurality of digital output signals 236, 238, 240, 242, 244, 246, and 248 are generated by analog-to-digital converters 124, 126, 128, 130, 132, 134, and 136, respectively. A digital value of a digital output signal generated by an analog-to-digital converter represents an amplitude of energy of a pulse of an amplified output signal. For example, a digital value of digital output signal 234 output by analog-to-digital converter 122 is a value of an amplitude of a pulse of amplified output signal 216. Each pulse is generated by an X-ray quantum, such as an X-ray photon.

An adder of a spectrum memory circuit adds a number of pulses in a digital output signal. For example, when analog-to-digital converter 122 converts a pulse of amplified output signal 216 into digital output signal 234 to determine an amplitude of the pulse of amplified output signal 216, an adder within spectrum memory circuit 140 increments, by one, a value within a memory device of spectrum memory circuit 140. Accordingly, at an end of an X-ray examination of substance 82, a memory device within a spectrum memory circuit stores a number of X-ray quanta detected by a detector element. For example, a memory device within spectrum memory circuit 142 stores a number of X-ray photons detected by detector element 24 and each of the X-ray photons has an amplitude of energy or alternatively an amplitude of intensity that is determined by analog-to-digital converter 124.

A correction device receives a number of X-ray quanta that have a range of energies and are stored within a memory device of one of spectrum memory circuits 140, 142, 144, 146, 148, 150, 152, and 154, and divides the number of X-ray quanta by a number of X-ray quanta having the range of energies received from a memory device of spectrum memory circuit 138. For example, correction device 156 receives a number of X-ray photons having a range of energies from a memory device of spectrum memory circuit 140, and divides the number of X-ray photons by a number of X-ray photons having the range received from a memory device of spectrum memory circuit 138. Each correction device outputs a correction output signal that represents a range of energies within X-ray quanta received by a detector element. For example, correction device 156 outputs a correction output signal 280 representing an energy spectrum or alternatively an intensity spectrum within X-ray quanta detected by detector element 22. As another example, correction device 158 outputs correction output signal 282 representing an energy spectrum within X-ray quanta detector element 24. Similarly, a plurality of correction output signals 284, 286, 288, 290, 292, and 294 are generated by correction devices 160, 162, 164, 166, 168, and 170, respectively.

It is noted that a number of pulse-height shaper amplifiers 104, 106, 108, 110, 112, 114, 116, and 118 changes with a number of scatter detector elements 22, 24, 26, 28, 30, 32, 34, and 36. For example, five pulse-height shaper amplifiers are used for amplifying signals received from five corresponding scatter detector elements. As another example, four pulse-height shaper amplifiers are used for amplifying signals received from corresponding four scatter detector elements. Similarly, a number of analog-to-digital converters 120, 122, 124, 126, 128, 130, 132, 134, and 136 changes with a number of detector elements 20, 22, 24, 26, 28, 30, 32, 34, and 36 and a number of spectrum memory circuits 138, 140, 142, 144, 146, 148, 150, 152, and 154 changes with the number of detector elements 20, 22, 24, 26, 28, 30, 32, 34, and 36.

Processor 190 receives correction output signals 280, 282, 284, 286, 288, 290, 292, and 294 to generate a momentum transfer x, measured in inverse nanometers ($nm^{-1}$), from an energy spectrum r(E) of energy E of X-ray quanta within scattered radiation detected by scatter detector 18 (shown in FIG. 1). Processor 190 generates the momentum transfer x by applying $$x = (E/hc)\sin(\theta/2) \qquad \text{Eq. (1)}$$

where c is a speed of light, h is Planck's constant, and θ represents a constant scatter angle of X-ray quanta of scattered radiation detected by scatter detector 18. An example of θ includes scatter angle 89 (shown in FIG. 1). Processor 190 relates the energy E to the momentum transfer x by Eq. (1). Mechanical dimensions of secondary collimator 76 (shown in FIG. 1) define the scatter angle θ. The secondary collimator 76 restricts scattered radiation that does not have the scatter angle θ. Processor 190 receives the scatter angle θ from a user, such as a human being, via input device 192. Processor 190 generates a diffraction profile of substance 82 (shown in FIG. 1) by calculating a number of scatter X-ray photons that are detected by scatter detector 18 and by plotting the number of scatter X-ray photons versus the momentum transfer x.

Figure 3:
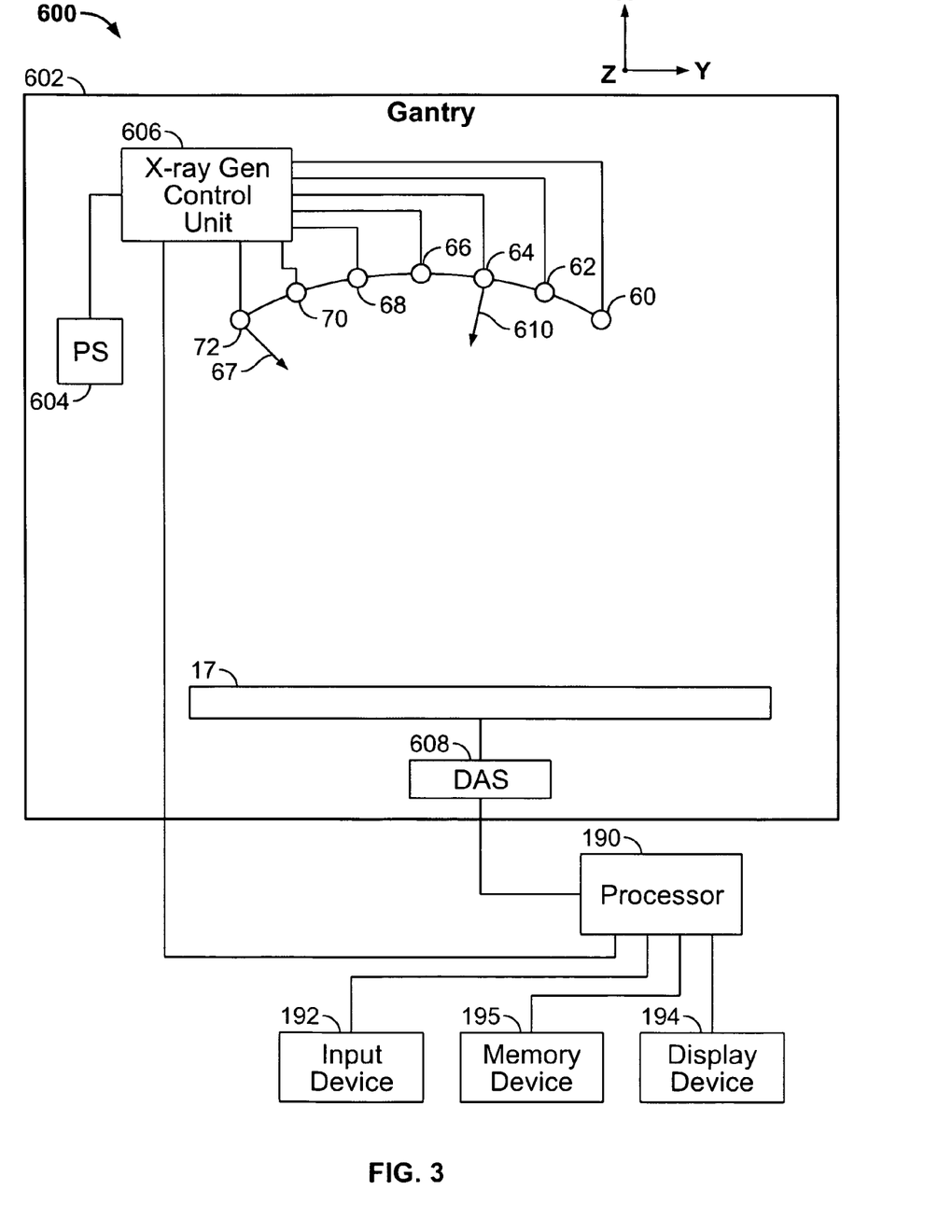
FIG. 3 is a block diagram of an embodiment of a system for generating an X-ray image.

FIG. 3 is a block diagram of an embodiment of a system 600 for characterizing a substance. System 600 includes a gantry 602, processor 190, input device 192, display device 194, and memory device 195. Gantry 602 is an example of gantry 12 (shown in FIG. 1). Gantry 602 includes a power supply 604, an X-ray generation control unit 606, X-ray sources 60, 62, 64, 66, 68, 70, and 72, a data acquisition system (DAS) 608, and transmission detector 17. Alternatively, power supply 604 is located outside gantry 602.

X-ray generation control unit 606 includes a pulse generator (not shown) that is coupled to processor 190 and that receives power from power supply 604. Power supply 604 is coupled to X-ray sources 60, 62, 64, 66, 68, 70, and 72 to supply power to X-ray sources 60, 62, 64, 66, 68, 70, and 72.

Processor 190 issues a command, such as a first on command, a second on command, a first off command, and/or a second off command. Upon receiving the first on command from processor 190, the pulse generator generates a pulse and transmits the pulse to X-ray source 72. Upon receiving a pulse from the pulse generator, X-ray source 72 generates X-ray beam 67 under a potential applied by power supply 604. Similarly, upon receiving the first off command signal from processor 190, the pulse generator stops transmitting a pulse to X-ray source 72 and X-ray source 72 stops generating X-ray beam 67. Furthermore, upon receiving the second on command signal from processor 190, the pulse generator generates and transmits a pulse to any one of the remaining X-ray sources 60, 62, 64, 66, 68, and 70, and any one of the remaining X-ray sources 60, 62, 64, 66, 68, and 70 generates an X-ray beam. For example, upon receiving the second on command signal from processor 190, the pulse generator generates and transmits a pulse to X-ray source 64 and X-ray source 64 generates an X-ray beam 610. In this example, upon receiving the second off command signal from processor 190, the pulse generator stops transmitting a pulse to X-ray source 64, and X-ray source 64 stops generating X-ray beam 610.

DAS 608 receives electrical output signals, including electrical output signal 196 (shown in FIG. 2), output by detector elements, including detector elements 20 and 21, of transmission detector 17 at x-axis position 107, samples the electrical output signals, and converts the samples to a plurality of digital signals for subsequent processing. Processor 190 receives sampled and digitized data from DAS 608 when transmission detector 17 is at x-axis position 107 and performs image reconstruction on the data to generate an X-ray image, such as a CT image, of substance 82. In one embodiment, processor 190 displays an X-ray image on display device 194 and/or stores the X-ray image in memory device 195. An X-ray image includes a plurality of CT numbers measured in Hounsfeld units (HUs). Each pixel in an X-ray image is represented by a CT number.

Figure 4:
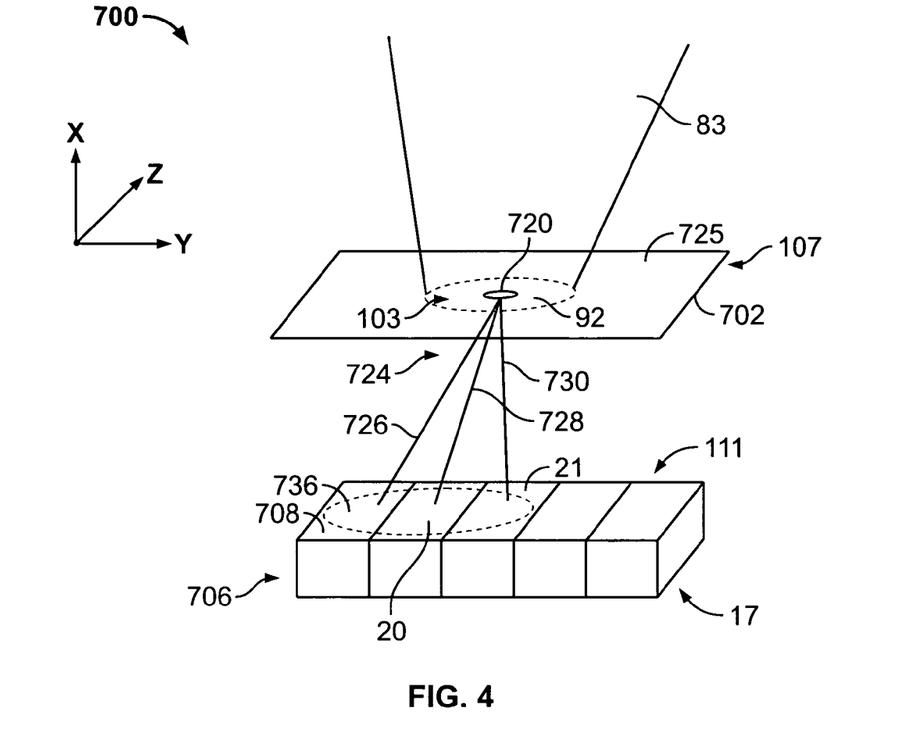
FIG. 4 is an isometric view of an alternative embodiment of a system for improving a spatial resolution of an image.

FIG. 4 is an isometric view of an embodiment of a system 700 for improving a spatial resolution of an image. System 700 is similar to system 10 except that a plate 702 is located at the same x-axis position 107 as that of transmission detector 17 in system 10. For example, if transmission detector 17 is located in system 10 at a distance, parallel to the x-axis, of H mm from the origin, plate 702 is also located at the distance of H mm from the origin in system 700, where H is a rational number. Plate 702 is located in a yz plane. Transmission detector 17 is not placed at x-axis position 107 in system 700. Instead, transmission detector 17 is placed within system 700 at an x-axis position 706, along the x-axis farther than x-axis position 107 from the origin. Moreover, transmission detector 17 is placed at the same y-axis position, along the y-axis with respect to the origin, in system 700 as the y-axis position in system 10. Furthermore, transmission detector 17 is placed at the same z-axis position, along the z-axis with respect to the origin, in system 700 as the z-axis position in system 10. Transmission detector 17 includes a plurality of detector elements including detector elements 20, 21, and 708.

In one embodiment, transmission detector 17 has a pitch that ranges from and includes 0.20 mm to 0.30 mm. For example, transmission detector 17 has a pitch of 0.2 mm. As another example, transmission detector 17 has a pitch of 0.25 mm. As yet another example, transmission detector 17 has a pitch of 0.3 mm. A pitch of transmission detector 17 is a distance, parallel to the y-axis, between centroids of adjacent detector elements of transmission detector 17. For example, a pitch of transmission detector 17 is a distance, parallel to the y-axis, between a centroid of detector element 708 and a centroid of detector element 20.

Transmission detector 17 is a one-dimensional pixellated detector that is pixellated in the y direction. Each detector element of transmission detector 17 is a pixel, and includes a scintillator and a photodiode. Each detector element of transmission detector 17 records radiation incident in the detector element independent of radiation that is incident on the remaining detector elements of transmission detector 17.

Plate 702 is made of an X-ray radiation absorbing material, such as lead or tungsten. Plate 702 defines and includes an aperture 720 located at position 103. An example of aperture 720 includes a pin-hole. Another example of an aperture in plate 702 includes a slit. Aperture 720 has a width, in the y-direction, ranging from and including 0.2 mm to 2 mm, and the width is less than a width of primary beam 83 at area 92 in the y-direction. As an example, aperture 720 has a width, in the y-direction, of 0.2 mm. As another example, aperture 720 has a width, in the y-direction, of 1 mm. As yet another example, aperture 720 has a width, in the y-direction, of 2 mm. Scatter detector 16 (shown in FIG. 1) may be placed in the same yz plane as that of transmission detector 17 placed in system 700 instead of the same yz plane as that of transmission detector 17 placed in system 10.

A surface 725 of plate 702 is at a focus of primary collimator 14 (shown in FIG. 1). For example, surface 725 is at a point of convergence of primary beam 83. As another example, a center of surface 725 is at a point of convergence of primary beam 83. Surface 725 faces container 79 (shown in FIG. 1).

Primary beam 83 passes through aperture 720, which selects a plurality of portions of primary beam 83 to pass through to output a plurality of beams 726, 728, and 730. Beams 726, 728, and 730 form a fan beam 724. An area 736, which is a focal spot, encompassed by fan-beam 724 on surface 111 is greater than area 92 (shown in FIG. 1). Area 736 is shown in dotted lines. Detector elements 20, 21, and 708 detect beams 726, 728, and 730, respectively to output a plurality of electrical output signals. Unlike primary beam 83 incident on area 92 of detector element 20 in system 10 of FIG. 1, fan-beam 724 is incident on detector elements 20, 21, and 708 in the y direction.

DAS 608 (shown in FIG. 3) receives electrical output signals including electrical output signals output by detector elements 20, 21, and 708 of transmission detector 17 at x-axis position 706, samples the electrical output signals, and converts the samples to a plurality of digital signals for subsequent processing. Processor 190 (shown in FIG. 2) receives sampled and digitized data from DAS 608 when transmission detector 17 is at position 706 and performs image reconstruction on the data to generate an X-ray image, such as a CT image, of substance 82 (shown in FIG. 1). A spatial resolution of an X-ray image reconstructed from electrical signals output from transmission detector 17 at position 706 is higher than a spatial resolution of an X-ray image reconstructed from electrical signals output from transmission detector 17 at position 107 in system 10.

In another alternative embodiment, plate 702 includes a plurality of apertures. The number of apertures within plate 702 matches a number of foci of primary collimator 14. For example, if primary collimator 14 is a multi-focus primary collimator that outputs two primary beams that converge on two different foci on surface 725 of plate 14, plate 14 includes two apertures. In the example, a first one of the two primary beams converges onto a first focus of plate 14 and a second one of the two primary beams converges onto a second focus of plate 14. Moreover, in the example, a first one of the apertures receives the first primary beam and a second one of the two apertures receives the second primary beam. In yet another alternative embodiment, a higher or a lower number of detector elements than a number of detector elements 20, 21, and 708 detect a fan-beam output from aperture 720.

Figure 5:
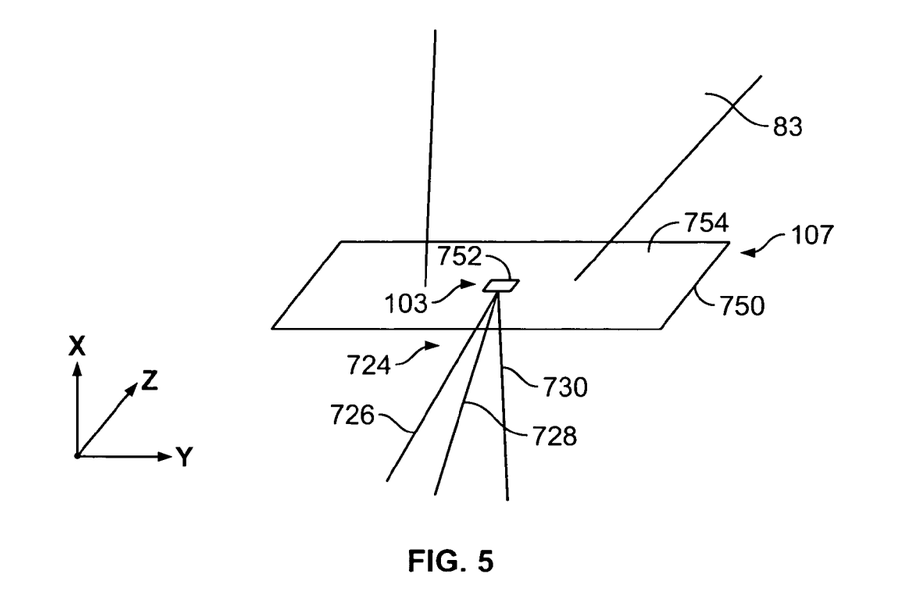
FIG. 5 is an isometric view of an embodiment of a plate that may be used within the system of FIG. 1.

FIG. 5 is an isometric view of an alternative embodiment of system 700 shown in FIG. 4. In this embodiment, a plate 750 is placed at position 107 instead of plate 702 (FIG. 4). Plate 750 has an aperture 752 having a square cross-section in a yz plane. Aperture 752 is located at position 103. A surface 754 of plate 750 is located at a focus of primary collimator 14. For example, a center of surface 754 is at a point of convergence of primary beam 83. As another example, surface 754 is at a point of convergence of primary beam 83. Surface 754 faces container 79 (shown in FIG. 1). When primary beam 83 passes through aperture 752, aperture 752 allows portions of primary beam 83 to pass through to output beams 726, 728, and 730.

In an alternative embodiment, instead of aperture 752, plate 750 includes an aperture having a cross-section in a yz plane of a shape other than the square cross-section. For example, plate 750 includes an aperture having a rectangular cross-section in a yz plane. In yet another alternative embodiment, plate 750 includes an aperture having a cross-section in a yz plane that is polygonal or curved or a combination of a polygon and a curve.

Figure 6:
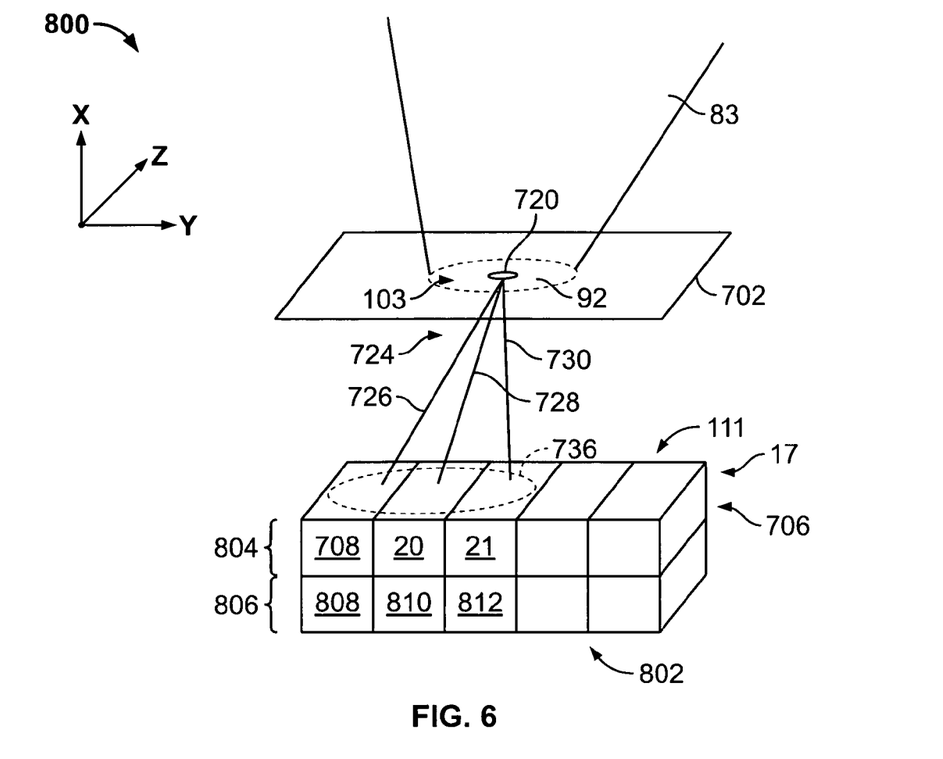
FIG. 6 is an isometric view of another alternative embodiment of a system for improving a spatial resolution of an image.

FIG. 6 shows an isometric view of an embodiment of a system 800 for improving a spatial resolution of an image. System 800 is similar to system 700, shown in FIG. 4, except that system 800 includes a dual-energy transmission detector 802. Dual-energy transmission detector 802 includes an embodiment of the previously described transmission detector 17, with detector elements 20, 21, and 708, as a transmission detector layer 804; and also includes a transmission detector layer 806. Transmission detector layer 806 includes a plurality of detector elements 808, 810, and 812. Transmission detector layer 804 of dual-energy transmission detector 802 is located at x-axis position 706 from the origin. Transmission detector layer 804 is adjacent to transmission detector layer 806. Transmission detector layer 804 is a low-energy resolving layer that is sensitive to X-ray radiation of low-energy, such as ranging from and including 30 kiloelectron volts (keV) to 60 keV. For example, detector elements 708 and 21 of transmission detector layer 804 detect beams 726 and 730, respectively, of the low-energy radiation. As another example, transmission detector layer 804 is sensitive to X-ray radiation of the low-energy equal to 30 keV. As yet another example, transmission detector layer 804 is sensitive to X-ray radiation of the low-energy equal to 45 keV. As still another example, transmission detector layer 804 is sensitive to X-ray radiation of the low-energy equal to 60 keV. Transmission detector layer 806 is a high-energy resolving layer that is sensitive to X-ray radiation of high-energy, such as ranging from 60 keV to 200 keV, that is higher than the low-energy radiation. For example, detector element 810 of transmission detector layer detects beam 728 of the high-energy radiation. As another example, transmission detector layer 806 is sensitive to X-ray radiation of the high-energy equal to 62 keV. As yet another example, transmission detector layer 806 is sensitive to X-ray radiation of the high-energy equal to 120 keV. As still another example, transmission detector layer 806 is sensitive to X-ray radiation of the high-energy equal to 200 keV.

Transmission detector layer 806 is a one-dimensional pixellated layer extending in the y-direction. Each pixel of transmission detector layer 806 is a detector element and each detector element of transmission detector layer 806 detects X-rays incident independent of detection of X-rays by the remaining detector elements of transmission detector layer 806.

Figure 7:
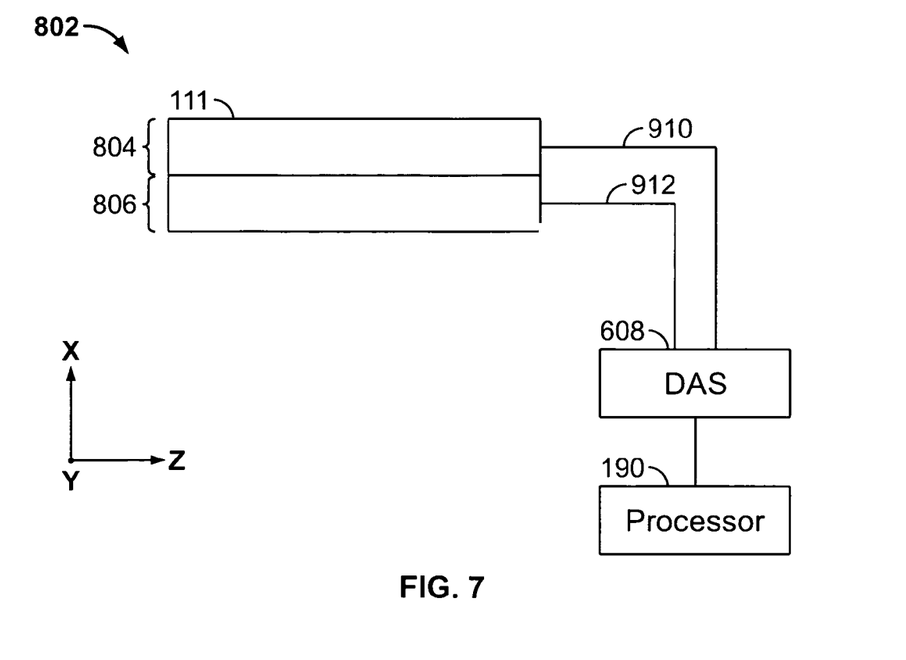
FIG. 7 is a side view of an embodiment of a dual-energy transmission detector that is used within the system of FIG. 6.

FIG. 7 shows a side view of an embodiment of dual-energy transmission detector 802. Transmission detector layer 804 detects beams 726 and 730 (shown in FIG. 6) to output a set 910 of electrical output signals. Similarly, transmission detector layer 806 detects beam 728 (shown in FIG. 6) to output a set 912 of electrical output signals. DAS 608 receives sets 910 and 912 of electrical output signals, samples the electrical output signals, and converts the samples to a plurality of digital signals for subsequent processing. Processor 190 receives sampled and digitized data, representing electrical output signals within sets 910 and 912, from DAS 608 and performs image reconstruction on the data to generate an X-ray image of substance 82.

Processor 190 determines a Photoelectric pathlength $A_{sub}^P$ of substance 82 and a Compton pathlength $A_{sub}^C$ of substance 82 (shown in FIG. 1) from sets 910 and 912. An example of determining Photoelectric and Compton pathlengths from electrical signals output by a dual-energy transmission detector is described in a paper, Robert E. Alvarez and Albert Macovski, Energy-selective Reconstructions in X-ray Computerized Tomography, Phys. Med. Biol., 1976, Vol. 21, No. 5, 733-744 (1976). Processor 190 derives the Photoelectric pathlength $A_{sub}^P$ and the Compton pathlength $A_{sub}^C$ from sampled and digitized data representing dual-energy electrical output signals, such as sets 910 and 912, when a function $f_P(E)$ representing Photoelectric energy dependence and a function $f_C(E)$ representing Compton energy dependence are known. A user provides the functions $f_P(E)$ and $f_C(E)$ via input device 192 (shown in FIG. 2) to processor 190.

A technical effect of the herein described systems for improving a spatial resolution of an image includes changing a position of transmission detector 17 from x-axis position 107 in system 10 to x-axis position 706 in system 700, and adding plate 702. The change in the position of transmission detector 17 and the addition of plate 702 results in detection by multiple detector elements, such as detector elements 20, 21, and 708. The detection by multiple detector elements improves the spatial resolution. Another technical effect includes determining the photoelectric and Compton pathlengths by using dual-energy transmission detector 802. The Photoelectric pathlength and the Compton pathlength $A_{sub}^C$ are used to correct a set of attenuation artifacts that are generated in determining a molecular interference function, which is a characteristic of substance 82. A description of the molecular interference function is provided in a United States Patent Application Publication Number US20070263772A1, with Ser. No. 11/434,486, filed on May 15, 2006, and titled "Systems and Methods For Determining A Packing Fraction of a Substance".

Exemplary embodiments of systems for improving a spatial resolution of an image are described above in detail. The systems are not limited to the specific embodiments described herein. For example, the systems may be used in combination with other inspection or detection systems.

While various embodiments of the invention have been described, those skilled in the art will recognize that modifications of these various embodiments of the invention can be practiced within the spirit and scope of the claims.

What is claimed is:

1. A system for improving a spatial resolution of an image, said system comprising:
    an X-ray source directed toward a plurality of focal points, said X-ray source configured to generate an X-ray beam that converges at a first focal point of the plurality of focal points;
    a transmission detector configured to detect the X-ray beam to output a plurality of electrical signals; and
    a plate positioned with respect to said transmission detector, said plate configured to interact with the X-ray beam at the first focal point and output a fan-beam upon interacting with the X-ray beam.

2. A system in accordance with claim 1, wherein said plate defines an aperture configured to interact with the X-ray beam to output the fan-beam.

3. A system in accordance with claim 2, further comprising a primary collimator, wherein the aperture is located at a focus of the primary collimator.

4. A system in accordance with claim 1, wherein said transmission detector comprises a plurality of detector elements, each detector element of said plurality of detector elements corresponding to one pixel of a plurality of pixels, said plurality of pixels configured to detect the fan-beam.

5. A system in accordance with claim 1, further comprising a primary collimator configured to collimate X-rays into the X-ray beam, said plate defining an aperture configured to select a portion of the X-ray beam to generate the fan-beam.

6. A system in accordance with claim 1, wherein said plate is positioned in a plane parallel to a plane of said transmission detector.

7. A system in accordance with claim 1, wherein said transmission detector comprises a dual-energy transmission detector.

8. A system for improving a spatial resolution of an image, said system comprising:
    an X-ray source directed toward at least one focal point, said X-ray source configured to generate an X-ray beam that converges at the at least one focal point of the plurality of focal points;
    a transmission detector configured to detect the X-ray beam; and
    a plate positioned between said X-ray source and said transmission detector, said plate configured to output a plurality of beams from the at least one focal point upon interacting with the X-ray beam.

9. A system in accordance with claim 8, wherein said plate defines an aperture configured to interact with the X-ray beam to output the plurality of beams.

10. A system in accordance with claim 9, further comprising a primary collimator, wherein the aperture is located at a focus of the primary collimator.

11. A system in accordance with claim 8, wherein said transmission detector comprises a plurality of detector elements, each detector element of said plurality of detector elements corresponding to one pixel of a plurality of pixels, said plurality of pixel configured to detect the plurality of beams.

12. A system in accordance with claim 8, further comprising a primary collimator configured to collimate X-rays into the X-ray beam, said plate defining an aperture configured to select a portion of the X-ray beam to generate the plurality of beams.

13. A system in accordance with claim 8, wherein said plate is positioned in a plane parallel to a plane of said transmission detector.

14. A system in accordance with claim 8, wherein said transmission detector comprises a dual-energy transmission detector.

15. A system for improving a spatial resolution of an image, said system comprising:
    a plurality of X-ray sources arranged along an arc and configured to generate at least one X-ray beam that is incident on a substance, the at least one X-ray beam converging at a focal point;
    a transmission detector configured to detect the at least one X-ray beam; and
    a plate positioned between the substance and said transmission detector at the focal point, said plate configured to output a plurality of beams at the focal point upon interacting with the X-ray beam.

16. A system in accordance with claim 15, wherein said plate defines an aperture configured to interact with the X-ray beam to output the plurality of beams.

17. A system in accordance with claim 15, wherein said transmission detector comprises a plurality of detector elements, each detector element of said plurality of detector elements corresponding to one pixel of a plurality of pixels, said plate directing the plurality of beams to said plurality of pixels.

18. A system in accordance with claim 15, further comprising a primary collimator configured to collimate X-rays into the at least one X-ray beam, said plate defining an aperture configured to select a portion of the at least one X-ray beam to generate the plurality of beams.

19. A system in accordance with claim 15, wherein said plate is positioned in a plane parallel to a plane of said transmission detector.

20. A system in accordance with claim 15 wherein said plurality of X-ray sources are configured to generate a first X-ray beam and a second X-ray beam, said plate comprising:
    a first aperture configured to interact with the first X-ray beam to generate a first plurality of beams; and
    a second aperture configured to interact with the second X-ray beam to generate a second plurality of beams.

* * * * *